(12) United States Patent
Jaseer et al.

(10) Patent No.: US 11,529,622 B2
(45) Date of Patent: Dec. 20, 2022

(54) CATALYST SYSTEMS

(71) Applicants: Saudi Arabian Oil Company, Dhahran (SA); King Fahd University of Petroleum and Minerals, Dhahran (SA)

(72) Inventors: E A Jaseer, Dhahran (SA); Samir Barman, West Bengal (IN); Nestor Garcia Villalta, Saragossa (ES); Motaz Khawaji, Thuwal (SA); Wei Xu, Thuwal (SA)

(73) Assignees: Saudi Arabian Oil Company, Dhahran (SA); King Fahd University of Petroleum and Minerals, Dhahran (SA)

(*) Notice: Subject to any disclaimer, the term of this patent is extended or adjusted under 35 U.S.C. 154(b) by 0 days.

(21) Appl. No.: 17/532,257

(22) Filed: Nov. 22, 2021

(65) Prior Publication Data

US 2022/0288573 A1    Sep. 15, 2022

Related U.S. Application Data

(60) Provisional application No. 63/160,067, filed on Mar. 12, 2021.

(51) Int. Cl.
| | | |
|---|---|---|
| *B01J 31/24* | (2006.01) | |
| *B01J 31/22* | (2006.01) | |
| *B01J 31/14* | (2006.01) | |
| *C07C 2/36* | (2006.01) | |

(52) U.S. Cl.
CPC ......... *B01J 31/2409* (2013.01); *B01J 31/143* (2013.01); *B01J 31/2234* (2013.01); *C07C 2/36* (2013.01); *B01J 2231/20* (2013.01); *B01J 2531/62* (2013.01); *C07C 2531/14* (2013.01); *C07C 2531/22* (2013.01); *C07C 2531/24* (2013.01)

(58) Field of Classification Search
None
See application file for complete search history.

(56) References Cited

U.S. PATENT DOCUMENTS

| | | |
|---|---|---|
| 2,738,151 A | 3/1956 | Herzog |
| 3,061,602 A | 10/1962 | Duck et al. |
| 3,686,350 A | 8/1972 | Yamada et al. |
| 4,242,531 A | 12/1980 | Carter |
| 4,484,016 A | 11/1984 | Maschmeyer et al. |
| 4,528,415 A | 7/1985 | Knudsen |
| 4,532,370 A | 7/1985 | Le Quan et al. |
| 4,538,018 A | 8/1985 | Carter |
| 4,606,854 A | 8/1986 | Ozawa et al. |
| 4,615,998 A | 10/1986 | Le Quan et al. |
| 5,292,837 A | 3/1994 | Heinrich et al. |
| 5,376,706 A | 12/1994 | Barsotti et al. |
| 5,494,171 A | 2/1996 | Kazamoto et al. |
| 5,728,912 A | 3/1998 | Saqualain Haider Rizvi et al. |
| 5,792,895 A | 8/1998 | Commereuc et al. |
| 5,811,618 A | 9/1998 | Wu |
| 5,856,612 A | 1/1999 | Araki et al. |
| 5,877,376 A | 3/1999 | Commereuc et al. |
| 6,184,428 B1 | 2/2001 | Zahoor et al. |
| 6,767,975 B1 | 7/2004 | Liu |
| 6,903,042 B2 | 6/2005 | Drochon et al. |
| 7,122,497 B1 | 10/2006 | Nagy et al. |
| 7,157,532 B2 | 1/2007 | Payer et al. |
| 7,297,832 B2 | 11/2007 | Blann et al. |
| 7,300,904 B2 | 11/2007 | Dixon et al. |
| 7,329,635 B2 | 2/2008 | Dickakian et al. |
| 7,361,623 B2 | 4/2008 | Dixon et al. |
| 7,638,597 B2 | 12/2009 | Etherton et al. |
| 7,919,569 B2 | 4/2011 | Xu et al. |
| 7,964,763 B2 | 6/2011 | Dixon et al. |
| 8,227,653 B2 | 7/2012 | Weber et al. |
| 8,252,871 B2 | 8/2012 | Aliyev et al. |
| 10,280,125 B2 | 5/2019 | Sogo et al. |

(Continued)

FOREIGN PATENT DOCUMENTS

| | | |
|---|---|---|
| CN | 101189270 A | 5/2008 |
| CN | 102807632 A | 12/2012 |

(Continued)

OTHER PUBLICATIONS

Jiang et al., "A series of novel bisphosphinoamine ligands: Synthesis, characterization and application in ethylene tetramerization", Chinese Sci Bull Nov. 2010 vol. 55 No.33. (Year: 2010).*

Notification of Transmittal of the International Search Report and the Written Opinion of the International Searching Authority, or the Declaration dated Mar. 15, 2022 pertaining to International application No. PCT/US2021/061123 filed Nov. 30, 2021, 20 pages.

Notification of Transmittal of the International Search Report and the Written Opinion of the International Searching Authority, or the Declaration dated Mar. 11, 2022 pertaining to International application No. PCT/US2021/061117 filed Nov. 30, 2021, 23 pages.

(Continued)

*Primary Examiner* — Ali Z Fadhel

(74) *Attorney, Agent, or Firm* — Dinsmore & Shohl LLP

(57) ABSTRACT

Catalyst systems suitable for tetramerizing ethylene to form 1-octene may include a catalyst including a chromium compound coordinated with a ligand and a co-catalyst including an organoaluminum compound. The ligand may have a chemical structure: $(R_1)(R_2)A$-$X$—$C(R_3)(R_4)$. A and C may be phosphorus. X may be $B(R_5)$, $Si(R_5)_2$, $N(R_5)$, wherein $R_5$ is an aryl group substituted with a halogen, halogenated alkyl or a silyl group, and wherein B, or N, or Si is bound to A and C. $R_1$, $R_2$, $R_3$, and $R_4$ may be independently chosen hydrocarbyl groups or heterohydrocarbyl groups.

20 Claims, No Drawings

(56) References Cited

U.S. PATENT DOCUMENTS

| | | | |
|---|---|---|---|
| 10,471,416 | B2 | 11/2019 | Im et al. |
| 11,104,621 | B2 | 8/2021 | Khawaji et al. |
| 2003/0109766 | A1 | 6/2003 | Commereuc et al. |
| 2004/0259720 | A1 | 12/2004 | Sato et al. |
| 2005/0288470 | A1 | 12/2005 | Benham et al. |
| 2007/0027276 | A1 | 2/2007 | Cann et al. |
| 2009/0105488 | A1 | 4/2009 | Cheng et al. |
| 2010/0113257 | A1 | 5/2010 | Kreishcher et al. |
| 2010/0190939 | A1 | 7/2010 | Fritz et al. |
| 2010/0274065 | A1 | 10/2010 | Sydora |
| 2012/0029258 | A1 | 2/2012 | Al-Masned et al. |
| 2012/0172645 | A1 | 7/2012 | Sydora |
| 2013/0123443 | A1 | 5/2013 | Siraux et al. |
| 2013/0303817 | A1 | 11/2013 | Shaik et al. |
| 2014/0088331 | A1 | 3/2014 | Rolland |
| 2014/0250835 | A1 | 9/2014 | Prabhu et al. |
| 2015/0087873 | A1 | 3/2015 | Overett et al. |
| 2015/0141605 | A1 | 5/2015 | Bradin |
| 2016/0122371 | A1 | 5/2016 | Lee et al. |
| 2016/0311950 | A1 | 10/2016 | Batinas-Geurts et al. |
| 2016/0367977 | A1 | 12/2016 | Shaikh et al. |
| 2017/0197892 | A1 | 7/2017 | Khawaji et al. |
| 2017/0274356 | A1 | 9/2017 | Cann et al. |
| 2019/0308179 | A1 | 10/2019 | Lee et al. |

FOREIGN PATENT DOCUMENTS

| | | | |
|---|---|---|---|
| CN | 103665201 A | | 3/2014 |
| CN | 103724149 A | | 4/2014 |
| CN | 107778388 A | | 3/2018 |
| EP | 0135441 A1 | | 3/1985 |
| EP | 0181954 A1 | | 5/1986 |
| EP | 0221206 A1 | | 5/1987 |
| EP | 0352856 A1 | | 1/1990 |
| EP | 2738151 A1 | | 6/2014 |
| EP | 3536696 A1 | | 9/2019 |
| EP | 3640232 A1 | | 4/2020 |
| EP | 3805240 A1 | | 4/2021 |
| JP | H0288529 A | | 3/1990 |
| RU | 2561921 C1 | | 9/2015 |
| WO | 2010092554 A1 | | 8/2010 |
| WO | 2012013805 A1 | | 2/2012 |
| WO | 2013154446 A1 | | 10/2013 |
| WO | 2013168106 A1 | | 11/2013 |
| WO | 2015087303 A2 | | 6/2015 |
| WO | 2015087304 A2 | | 6/2015 |
| WO | 2015087305 A2 | | 6/2015 |
| WO | 2015118462 A1 | | 8/2015 |
| WO | 2017120310 A1 | | 7/2017 |
| WO | 2018106764 A1 | | 6/2018 |
| WO | 2019235799 A1 | | 12/2019 |

OTHER PUBLICATIONS

Kim, Eun Ho et al. "Methylaluminoxane-Free Chromium Catalytic System for Ethylene Tetramerization", ACS Omega, vol. 2, No. 3, Mar. 31, 2017, pp. 765-773.
Wang, Tao et al. "Mixed aluminoxanes: efficient cocatalysts for bisphosphineamine/Cr(III) catalyzed ethylene tetramerization toward 1-octene", Applied Petrochemical Research, vol. 5, No. 2, Mar. 1, 2015, pp. 143-149.
AlJaralla et al. "Dimerization of Ethylene to Butene-1" Catalysis Today, 14 (1992) 1-124, 121 pgs.
Bariashier et al. "Recent advances in homogeneous chromium catalyst design for ethylene tri-, tetra-, oligo- and polymerization" Coordination Chemistry Reviews 385 (2019) 208-229, 22 pgs.
Bartlett et al. "Triptycene (9,10-o-Benzenoanthracene)" Contribution from the Converse Memorial Laboratory of Harvard University, Nov. 1942, 5 pgs.
Blann et al. "Ethylene tetramerisation: Subtle effects exhibited by N-substituted diphosphinoamine ligands" Journal of Catalysis 249 (2007) 244-249, 6 pgs.
Bollmann et al. "Ethylene Tetramerization: A New Route to Produce 1-Octene in Exceptionally High Selectivities" J. Am. Chem. Soc. 2004, 126, 2 pgs.
Elowe et al. "Nitrogen-Linked Diphosphine Ligands with Ethers Attached to Nitrogen for Chromium Catalyzed Ethylene Tri- and Tetramerizations" Arnold and Mabel Beckman Laboratories of Chemical Synthesis, 8 pgs.
Farrell "Developments in Linear Alpha Olefin (LAO) Comonomer Technologies for Polyethylene" Chemsystems PERP 2011S11, May 2012, 7 pgs.
Fei et al. "Influence of the functional group on the synthesis of aminophosphines, diphosphinoamines and iminobiphosphines" Dalton Trans., 2003, 2772-2779, 8 pgs.
Forestiere et al. "Oligomerization of Monoolefines by Homgeneous Catalysts" Oil & Gas Science and Technology—Rev. IFP, vol. 64 (2009) No. 6, 19 pgs.
Hennico "Butene-1 is made from ethylene" Hydrocarbon Processing, Journal vol. 69:3, 1990, Abstract Only, 2 pgs.
Karin et al. "Removal of Trace Elemental Impurities from Polyethylene by Nitric Acid" Analytical Chemistry, vol. 47, No. 13, Nov. 1975, 4 pgs.
Killian et al. "The use of bis(diphenylphosphino)amines with N-aryl functionalities in selective ethylene tri- and tetramerisation" Journal of Molecular Catalysis A: Chemical 270 (2007) 214-218, 5 pgs.
Kim et al. "Ligand Modification for Selectivity Control in Selective Ethylene Oligomerization" Macromol. Res., 26(4), 341-345 (2018), 5 pgs.
Kim et al. "MAO-free and extremely active catalytic system for ethylene tetramerization" Appl Organometal Chem. 2019;33:e4829, 13 pgs.
Mole "Organoaluminium Compounds" Aust. J. Chem., 1966, 19, 381-6, 6 pgs.
Obrey et al. "A Lewis Base Promoted Alkyl/Alkoxide Ligand Redistribution: Reaction of [Me2Al(u-OCPh3)]2 with THF" Organometallics 2001, 20, 5119-5124, 6 pgs.
Pietrzykowski et al. "Reactions of methyl- and ethylaluminium compounds with alkoxyalcohols. The influence of alkoxyalchohol substituents on the structure of the complexes formed" Inorganica Chimica Acta 334 (2002) 385-394, 10 pgs.
Smith et al. "Ethylene Dimerization over Supported Titanium Alkoxides" Journal of Catalysis 105, 187-198 (1987), 12 pgs.
Sydora "Selective Ethylene Oligomerization" Organometallics 2019, 38, 997-1010, 14 pgs.
Weldman et al. "Triptycene-based copolyimides with tailored backbone rigidity for enhanced gas transport" Polymer 126 (2017) 314-232, 10 pgs.
Chinese First Office Action dated Nov. 6, 2019, pertaining to Chinese Patent Application No. 201680035981.0.
European Extended Search Report dated Dec. 20, 2019, pertaining to European Application No. 19188473.3.
India Examination Report dated Apr. 27, 2020, pertaining to Indian Patent Application No. 201837025980.
Translation of Japanese Office Action dated Jul. 8, 2020, pertaining to Japanese Patent Application No. 2017-565808.
Translation of Japanese Office Action dated Jan. 6, 2021, pertaining to Japanese Patent Application No. 2018-535418.
Translation of Russian Office Action dated Feb. 27, 2020, pertaining to Russian Patent Application No. 2018128919.
Final Office Action dated Feb. 25, 2021, pertaining to U.S. Appl. No. 15/181,923.
Final Office Action dated May 10, 2019, pertaining to U.S. Appl. No. 15/181,923.
Non-Final Office Action dated Aug. 20, 2020, pertaining to U.S. Appl. No. 15/181,923.
Non-Final Office Action dated Sep. 4, 2019, pertaining to U.S. Appl. No. 15/181,923.
Non-Final Office Action dated Dec. 13, 2018, pertaining to U.S. Appl. No. 15/181,923.
Invitation to Pay Additional Fees dated Sep. 15, 2016, pertaining to Int'l Patent Application No. PCT/US2016/037366.
International Search Report and Written Opinion dated Nov. 21, 2016, pertaining to Int'l Patent Application No. PCT/US2016/037366.

(56) References Cited

OTHER PUBLICATIONS

Final Office Action dated Feb. 28, 2020, pertaining to U.S. Appl. No. 15/393,865.
Final Office Action dated Aug. 10, 2018, pertaining to U.S. Appl. No. 15/393,865.
Notice of Allowance and Fees Due dated Apr. 28, 2021, pertaining to U.S. Appl. No. 15/393,865.
Non-Final Office Action dated Jan. 4, 2021, pertaining to U.S. Appl. No. 15/393,865.
Non-Final Office Action dated Jan. 11, 2019, pertaining to U.S. Appl. No. 15/393,865.
Non-Final Office Action dated Mar. 13, 2018, pertaining to U.S. Appl. No. 15/393,865.
International Search Report and Written Opinion dated Jun. 8, 2017, pertaining to Int'l Patent Application No. PCT/US2017/012299.
Non-Final Office Action dated Oct. 19, 2018, pertaining to U.S. Appl. No. 15/830,800.
International Search Report and Written Opinion dated Feb. 20, 2018, pertaining to Int'l Patent Application No. PCT/US2017/064841.
Notice of Allowance and Fees due dated Sep. 10, 2020, pertaining to U.S. Appl. No. 16/134,207.
Non-Final Office Action dated Mar. 30, 2020, pertaining to U.S. Appl. No. 16/134,207.
International Search Report and Written Opinion dated Jan. 3, 2019, pertaining to Int'l Patent Application No. PCT/US2018/051514.
International Search Report and Written Opinion dated Mar. 18, 2021, pertaining to Int'l Patent Application No. PCT/US2020/059974.
Singapore Office Action dated Aug. 10, 2020, pertaining to Singapore Patent Application No. 11201805653U.
International Search Report and Written Opinion dated Feb. 28, 2022 pertaining to International application No. PCT/US2021/060330 filed Nov. 22, 2021, 17 pages.
International Search Report and Written Opinion dated Mar. 1, 2022 pertaining to International application No. PCT/US2021/061115 filed Nov. 30, 2021, 20 pages.
International Search Report and Written Opinion dated Mar. 4, 2022 pertaining to International application No. PCT/US2021/061114 filed Nov. 30, 2021, 20 pages.
International Search Report and Written Opinion dated Mar. 4, 2022 pertaining to International application No. PCT/US2021/061116 filed Nov. 30, 2021, 20 pages.
Tao, Jiang et al., "A series of novel bisphosphinoamine ligands: Synthesis, characterization and application in ethylene tetramerization", Chinese Science Bulletin, Science China Press (SCP) and Springer, CN, vol. 55, No. 33, Nov. 1, 2010, pp. 3750-3754.
Database CA [Online] Chemical Abstracts Service, Columbus, Ohio, US; 2014, Sun, Yueming et al "Boron- and silicon-bridged bis(diphenylphosphino)-type ligands for chromium-catalyzed ethylene oligomerization", XP002805681, retrieved from STN Database accession No. 2014:525027 abstract & Sun, Yueming et al: "Boron- and silicon-bridged bis(diphenylphosphino)-type ligands for chromium-catalyzed ethylene oligomerization" Chinese Science Bulletin, 59(21), 2613-2617; ISSN: 1001-6538, 2014.
Baojun, Zhang et al., "Cr(III)-Based Catalyst System for Oligomerization of Ethylene to 1-Octene with High Selectivity", Chinese Journal of Catalysis, vol. 28, No. 4, Jan. 1, 2007, pp. 317-320.
Chen, Hongxia et al., "Effects of halide in homogeneous Cr(III)/PNP/MAO catalytic systems for ethylene tetramerization toward 1-octene", Journal of Molecular Catalysis A: Chemical, Elsevier, Amsterdam, NL, vol. 270, No. 1-2, May 7, 2007, pp. 273-277.

* cited by examiner

CATALYST SYSTEMS

CROSS REFERENCE TO RELATED APPLICATIONS

This application claims the benefit of and priority to U.S. Application Ser. No. 63/160,067 filed on Mar. 12, 2021, and entitled "Catalyst Systems," the entire contents of which are incorporated by reference in the present disclosure.

TECHNICAL FIELD

Embodiments of the present disclosure generally relate to chemical processing and, more particularly, catalyst systems utilized in such chemical processing.

BACKGROUND

Linear alpha-olefins ("LAOs") are typically produced via the cracking of refinery products or the non-selective oligomerization of ethylene, which results in a broad alpha-olefin distribution. Currently, there are several industrial processes that produce LAOS, such as the Shell Higher Olefin Process (SHOP), which has been in operation since 1977. SHOP employs a combination of oligomerization and olefin metathesis chemistries to produce a variety of LAOs using a nickel-based catalyst. INEOS, a global manufacturer of petrochemicals, has also developed a proprietary process for synthesizing a wide range of LAOs with the flexibility to change distributions of products to meet demand.

However, demand for LAOs is rising in North America, Western Europe, and Asia. In particular, demand for short chain alpha olefins, such as 1-octene and 1-hexene, is rising due to their significance to a number of specific applications. For example, 1-octene may be used to improve the rheological melt and solid resin properties of polyethylene. As a result, the main consumer of 1-octene is the industry responsible for the high-volume production of linear low-density polyethylene (LLDPE) and high-density polyethylene (HDPE), which expands each year. The content of 1-octene may be from 1% to 2% in HDPE, and as much as 30% in some LLDPE grades.

Based on this, 1-octene is a significant chemical feedstock that is in market demand. Aside from the processes discussed above, various catalysts have been developed for the tetramerization of ethylene to selectively form 1-octene. However, these catalysts have deficiencies in several respects such as selectivity of 1-octene and fouling polymers. Accordingly, improved catalysts, which are suitable for tetramerization of ethylene to selectively form 1-octene, are desired in the industry.

SUMMARY

Fouling, as described in the present disclosure, refers to the undesirable formation of polymers. Such polymers may form as side-products in the reaction of ethylene to form 1-octene when a catalyst system including chromium is used. However, as described in the present disclosure, it has been discovered that the utilization of a particular ligand, which may coordinate with chromium, may reduce fouling. Moreover, in some embodiments, the utilization of catalysts including the ligands may contribute to maintaining the selectivity of 1-octene, or even enhancing the selectivity of 1-octene, as compared with similar catalyst systems.

According to one or more embodiments, a catalyst system suitable for tetramerizing ethylene to form 1-octene may include a catalyst including a chromium compound coordinated with a ligand and a co-catalyst comprising an organoaluminum compound. The ligand may have a chemical structure: $(R_1)(R_2)A\text{-}X\text{---}C(R_3)(R_4)$. A and C may be phosphorus. X may be $B(R_5)$, $Si(R_5)_2$, $N(R_5)$, wherein $R_5$ is an aryl group substituted with a halogen, halogenated alkyl or a silyl group, and wherein B, or N, or Si is bound to A and C. $R_1$, $R_2$, $R_3$, and $R_4$ may be independently chosen hydrocarbyl groups or heterohydrocarbyl groups.

Additional features and advantages of the aspects of the present disclosure will be set forth in the detailed description that follows and, in part, will be readily apparent to a person of ordinary skill in the art from the detailed description or recognized by practicing the aspects of the present disclosure.

DETAILED DESCRIPTION

The present disclosure describes catalyst systems that may be utilized to produce 1-octene from ethylene via tetramerization. Also described are methods for utilizing such catalyst systems. The presently described catalyst systems may include a catalyst and a co-catalyst, which are described in detail. In one or more embodiments, the catalyst may include chromium and a ligand. The co-catalyst may include an organoaluminum compound.

In one or more embodiments, the catalyst systems described in the present disclosure may be used to selectively tetramerize ethylene to produce 1-octene, while reducing undesirable polymerization, sometimes referred to as "fouling." Fouling may occur at least partially due to the formation of solid polyethylene-based residues, which may reduce fluid flow and/or fully block or at least partially block fluids in a reactor system from flowing at a desired rate. Without being bound by any particular theory, it is believed that the incorporation of the ligand described in the present disclosure into the catalyst system reduces fouling while maintaining a suitable yield of 1-octene.

It should be understood that the catalyst systems described in the present disclosure may not completely eliminate fouling during a reaction. However, in one or more embodiments, these catalyst systems reduce fouling as compared with catalyst systems that do not include the ligand as described in the present disclosure. Additionally, it should be understood that while these catalyst systems may be useful for the catalysis of the oligomerization of ethylene, such as the tetramerization of ethylene to form 1-octene, they may also be useful for the catalysis of other chemical reactions. As a result, these catalyst systems should not be considered limited in their use to the tetramerization of ethylene to form 1-octene.

As used in the present disclosure, the term "catalyst" refers to any substance that increases the rate of a specific chemical reaction. Catalysts described in this disclosure may be utilized to promote various reactions, such as, but not limited to, the tetramerization of ethylene to form 1-octene. Catalysts are generally not consumed in a reaction, but as would be understood in the art, may have reduced catalytic activity over time and need to be replaced and/or regenerated.

As used in the present disclosure, the term "co-catalyst" (also referred to as an activator and/or scavenger) generally refers to any substance or chemical agent that brings about catalysis of a chemical reaction in conjunction with one or more catalysts. In some embodiments, a catalyst may have independent catalytic functionality, while in other embodiments the catalyst may only have substantial catalytic functionality when paired with a co-catalyst. It should be understood that the catalyst and co-catalyst may be, in some embodiments, bonded or formed in a complex, but in other embodiments are not bonded or present in a complex. Some co-catalysts may be said to "activate" a catalyst, which may increase catalytic functionality.

As used in the present disclosure, the term "catalyst system" refers to any catalytically functional collection of chemical species. In one or more embodiments, a catalyst system may include a catalyst and a co-catalyst. In some embodiments, a catalyst system may include additional components, such as, for example, additional co-catalysts or non-catalytic additives which may serve other purposes.

As used in the present disclosure, the term "independently chosen" means that the R groups, such as, $R_1$, $R_2$, and $R_3$, can be identical or different. For example, $R_1$, $R_2$, and $R_3$ may all be substituted alkyls; or $R_1$ and $R_2$ may be a substituted alkyl, and $R_3$ may be an aryl. The R group may contain heteronuclear atoms other than C and H, such as N and O. A chemical name associated with an R group is intended to convey the chemical structure that is recognized in the art as corresponding to that of the chemical name. As a result, chemical names are intended to supplement and illustrate, not preclude, the structural definitions known to those of skill in the art.

As used in the present disclosure, the term "reaction product" refers to a chemical species formed from the reaction of any two or more reactant species or reagents. A reaction product may result in a covalent or ionic bond, coordination, or other interaction between reactant species. In one or more embodiments, two or more reaction products may result from the reaction of the reactant species, and all of these possible produced chemical species are included in the reaction product.

When used to describe certain carbon atom-containing chemical groups, a parenthetical expression having the form "$(C_x-C_y)$" means that the unsubstituted form of the chemical group has from x carbon atoms to y carbon atoms, inclusive of x and y. For example, a $(C_1-C_{50})$ alkyl group is an alkyl group having from 1 to 50 carbon atoms in its unsubstituted form. In some embodiments and general structures, certain chemical groups may be substituted by one or more substituents. A substituted chemical group defined using the "$(C_x-C_y)$" parenthetical may contain more than y carbon atoms depending on the identity of any substituents. For example, a "$(C_1-C_{50})$ alkyl substituted with exactly one phenyl (—$C_6H_5$)" may contain from 7 to 56 carbon atoms. Thus, in general when a chemical group defined using the "$(C_x-C_y)$" parenthetical is substituted by one or more carbon atom-containing substituents, the minimum and maximum total number of carbon atoms of the chemical group is determined by adding to both x and y the combined sum of the number of carbon atoms from all of the carbon atom-containing substituents.

The term "substitution" means that at least one hydrogen atom (—H) bonded to a carbon atom or heteroatom of a corresponding unsubstituted compound or functional group is replaced by a substituent. Substituents may be any suitable functional group or radical that could replace a hydrogen atom bonded to a carbon atom or heteroatom of a corresponding unsubstituted compound. For example, substituents may include, but are not limited to, hydrocarbyls, cyclohydrocarbyls, aryls, halogens, and amines.

The term "—H" means a hydrogen or hydrogen radical that is covalently bonded to another atom. "Hydrogen" and "—H" are interchangeable, and unless clearly specified have identical meanings.

The term "hydrocarbyl" means a monovalent radical resulting from removal of any hydrogen atom from a hydrocarbon, including aromatic hydrocarbons, non-aromatic hydrocarbons, cyclic or acyclic hydrocarbons, saturated or unsaturated hydrocarbons, straight chain or branched chain hydrocarbons, with or without heteronuclear atoms and substituted or unsubstituted hydrocarbons.

The term "heterohydrocarbyl" refers to a hydrocarbyl, from which at least one carbon atom has been replaced with a heteroatom. Examples of heteroatoms include, without limitation, oxygen, nitrogen, sulfur, and phosphorus.

The term "cyclohydrocarbyl" means an aromatic or non-aromatic, cyclic hydrocarbyl having at least three carbon atoms, including monocyclic and polycyclic hydrocarbyls, fused and non-fused polycyclic hydrocarbyls, and bicyclic hydrocarbyls, non-aromatic saturated or unsaturated cyclic hydrocarbyls, and substituted or unsubstituted hydrocarbyls.

The term "aryl" means an aromatic hydrocarbon radical, in which the carbon atoms of the aromatic system may be substituted or unsubstituted. Aryls include monocyclic, bicyclic and tricyclic aromatic hydrocarbon radicals. A monocyclic aromatic hydrocarbon radical includes one aromatic ring; a bicyclic aromatic hydrocarbon radical has two rings; and a tricyclic aromatic hydrocarbon radical has three rings. When the bicyclic or tricyclic aromatic hydrocarbon radical is present, at least one of the rings of the radical is aromatic. The other ring or rings of the aromatic radical may be independently fused or non-fused and aromatic or non-aromatic. Non-limiting examples of aryls include phenyl; fluorenyl; tetrahydrofluorenyl; indacenyl; hexahydroindacenyl; indenyl; dihydroindenyl; naphthyl; tetrahydronaphthyl; and phenanthrenyl.

The term "alkyl" means a saturated hydrocarbon radical that may be linear or branched. Accordingly, the term "$(C_1-C_{20})$ alkyl" means a saturated linear or branched hydrocarbon radical of from 1 to 20 carbon atoms that is unsubstituted or substituted. Examples of unsubstituted ($C_1$-$C_{20}$) alkyl include methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted ($C_1$-$C_{20}$) alkyl include trifluoromethyl and trifluoroethyl.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents, one or more double and/or triple bonds optionally may be present in substituents. The term "unsaturated" means containing one or more carbon-carbon double bonds or carbon-carbon triple bonds, or (in heteroatom-containing groups) one or more carbon-nitrogen double bonds, carbon-phosphorous double bonds, or carbon-silicon double bonds, not including double bonds that may be present in substituents, if any, or in aromatic rings or heteroaromatic rings, if any.

As noted previously, the embodiments of the present disclosure are directed to a catalyst system suitable for tetramerizing ethylene to form 1-octene. In one or more embodiments, the catalyst system includes a catalyst. In some embodiments, the catalyst includes chromium. It should be understood that, as contemplated in the present disclosure, a catalyst that includes chromium may be any chemical compound that includes chromium and is catalytically functional for, without limitation, promoting the tetramerization of ethylene to from 1-octene.

In one or more embodiments, the catalyst includes a chromium compound and a ligand. It should be understood that the chromium complexes described herein, which may coordinate with one or more ligands, are not necessarily limited in structure, but include chromium. In some embodiments, the chromium compound includes an organic chromium salt, an inorganic chromium salt, a chromium coordination, a chromium organometallic complex, or combinations of these. In some embodiments, the chromium compound includes a chromium trichloride tris-tetrahydrofuran complex, (benzene)tricarbonyl chromium, chromium (III) octanoate, chromium (III) acetylacetonate, chromium hexacarbonyl, chromium (III) 2-ethylhexanoate, or combinations of these.

It should be understood that the ligands described herein, which may coordinate with chromium of the chromium complex are not necessarily limited in structure. However, in one or more embodiments, the ligand may have a structure according to formula (I):

$(R_1)(R_2)A-X-C(R_3)(R_4)$  Formula (I)

In formula (I), A and C are each phosphorus (P); X is a linking group between A and C; and $R_1$, $R_2$, $R_3$, and $R_4$ are independently chosen from any hydrocarbyl group or heterohydrocarbyl group. As used in the present disclosure, the term "linking group" refers to any chemical moiety that covalently bonds at least two other chemical moieties. For example, X may be a chemical moiety that covalently bonds the chemical moieties of A and C. In one or more embodiments, X may comprise one or more elements selected from Group IIIA, Group IVA, Group VA, and Group VIA. In one or more embodiments, X may be $B(R_5)$, $Si(R_5)_2$, or $N(R_5)$. $R_5$ may be an aryl group substituted with a halogen, halogenated alkyl, or a silyl group. In some embodiments, one or more of $R_1$, $R_2$, $R_3$, and $R_4$ may comprise aryl moieties. In some embodiments, $R_1$, $R_2$, $R_3$, and $R_4$ may be independently chosen from a benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl, or tetrahydrofuranyl group.

In some embodiments, $R_1$, $R_2$, and A or $R_3$, $R_4$, and C may be bonded such that a cyclic moiety is formed. In such embodiments A and C may be phosphorus such that a cyclic moiety including P is formed. For example, $R_1$, $R_2$, and A may be bonded such that a cyclic moiety including P is formed. Likewise, $R_3$, $R_4$, and C may be bonded such that a cyclic moiety including P is formed. In one or more embodiments, $R_1$, $R_2$, and P may form a phospholane group. In one or more embodiments, $R_3$, $R_4$, and P may form a phospholane group. As described herein, a "phospholane group" refers to a cyclic organophosphorous compound comprising a five membered ring including phosphorous and four carbon atoms. In some embodiments, the phospholane compound may be unsubstituted or may be substituted by one or more hydrocarbyl groups. Cyclic moieties that may be formed from $R_1$, $R_2$, and P or $R_3$, $R_4$, and P in some embodiments are depicted in formulas (II) to (IX).

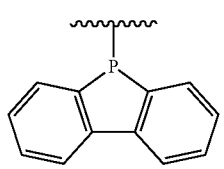

Formula (II)

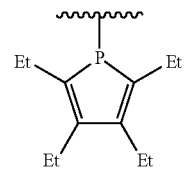

Formula (III)

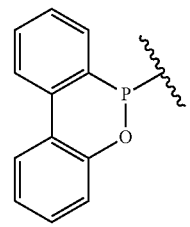

Formula (IV)

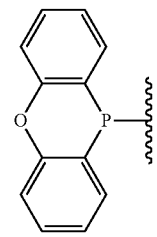

Formula (V)

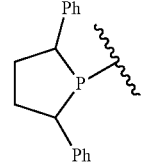

Formula (VI)

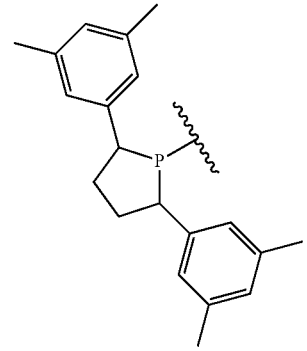

Formula (VII)

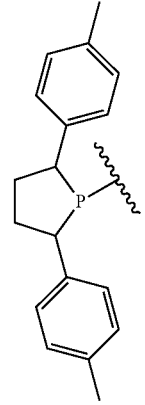

Formula (VIII)

-continued

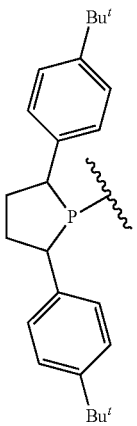

Formula (IX)

In one or more embodiments, X may be an organic linking group comprising —N(R$_5$)—, where R$_5$ is a substituted aryl group. The substituted aryl group, R$_5$, may be substituted with a halogenated alkyl or a silyl group. The halogenated alkyl group may be any alkyl group substituted with at least one halogen, including but not limited to fluorine, chlorine, bromine and iodine. In one or more embodiments, the halogenated alkyl group may be represented by the formula $C_nF_{2n+1}$. In one or more embodiments, the halogenated alkyl group is trifluoromethyl. As described herein, a "silyl group" has the general structure: $SiZ_3$, where each Z is independently chosen from a substituted or unsubstituted hydrocarbyl group or a substituted or unsubstituted heterohydrocarbyl group. In one or more embodiments, the substituted aryl group, R$_5$, may be substituted such that the substitution is in the meta position.

Without intending to be bound by theory, the electronic properties of the ligand, whether moieties of the ligand are electron donors or electron withdrawers, affect the binding strength of ethylene to the catalytic metal center. Additionally, the bulkiness of the ligand may introduce steric hindrances which also may affect the binding strength of ethylene to the metal center. Accordingly, the ligand may affect the reactivity and selectivity of the catalyst toward the formation of 1-octene.

In one or more embodiments, the ligand may be an N-aryl bisphosphineamine ligand. For example, in some embodiments, the ligand has a structure according to formula (X):

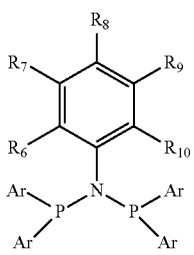

Formula (X)

In formula (X), each Ar is independently chosen from a substituted or unsubstituted aryl group; and R$_6$, R$_7$, R$_8$, R$_9$, and R$_{10}$ are each independently chosen from hydrogen (H) or a substituted or unsubstituted hydrocarbyl group. In one or more embodiments, one or more of R$_6$, R$_7$, R$_8$, R$_9$, and R$_{10}$ are a halogenated alkyl or silyl group. In some embodiments, one or more of R$_6$, R$_7$, R$_8$, R$_9$, and R$_{10}$ are groups represented formulaically as $C_nF_{2n+1}$. In some embodiments, one or more of R$_6$, R$_7$, R$_8$, R$_9$, and R$_{10}$ are groups represented formulaically as $SiZ_3$, where each Z is independently chosen from a substituted or unsubstituted hydrocarbyl group or a substituted or unsubstituted heterohydrocarbyl group. In one or more embodiments, at least one of R$_7$ or R$_9$ is a halogenated alkyl or silyl group. For example, in some embodiments, the ligand is $C_6H_4(m-CF_3)N(PPh_2)_2$. Without intending to be bound by theory, when the substitution is in the meta position, the electro-deficiency of the catalytic center is decreased such that ethylene is bound to form a cyclic intermediate, which favors the formation of 1-octene. The formation of 1-octene is shown in reaction scheme (I).

Reaction Scheme (I)

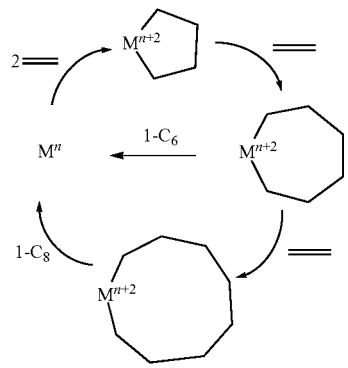

In one or more embodiments, the catalyst may include the ligand in an amount such that a molar ratio of the ligand to chromium in the catalyst is from 0.1 to 10.0.

The chromium compound and the ligand may be produced using procedures and methods known in the art. For example, procedures and methods for producing the chromium compound are described in U.S. Pat. No. 7,297,832, which is incorporated by reference in its entirety.

In one or more embodiments, the catalyst system also includes a co-catalyst. In some embodiments, the co-catalyst may include an organoaluminum compound. As described in the present disclosure, the term "organoaluminum compound" refers to any chemical compound that includes at least one aluminum atom and any organic moiety. It should be appreciated that the organoaluminum compound may include several chemical species, or may be a single chemical species. In some embodiments, the organoaluminum compound may be an alkyl aluminum compound. The aluminum alkyl compound may, for example, have a structure according to formula (XI):

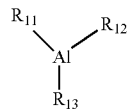

Formula (XI)

In formula (XI), R$_{11}$, R$_{12}$ and R$_{13}$ are each independently chosen from a hydrogen atom or a (C$_1$-C$_{20}$) hydrocarbyl group or a (C$_1$-C$_{20}$) heterohydrocarbyl group. In embodiments, the (C$_1$-C$_{20}$) hydrocarbyl group may be a substituted or unsubstituted (C$_1$-C$_{20}$) linear or branched hydrocarbyl group. In one or more embodiments, $R_{11}$, $R_{12}$ and $R_{13}$ may each be a hydrogen or a linear or branched ($C_1$-$C_{20}$) alkyl group. In some embodiments, the alkyl aluminum compound may be an aluminoxane structure (a partial hydrolysate of a trialkylaluminum compound). For example, suitable aluminum alkyl compounds may include trimethylaluminium, triethylaluminum, tripropylaluminum, tri-iso-butylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), and modified alkylaluminoxanes, such as modified methylaluminoxane (MMAO). As described in the present disclsoure, the term "modified alkylaluminoxane" refers to an alkylaluminoxane that includes one or more modifier groups, such as isobuytyl or n-octyl groups in addition to the alkyl groups. In one or more embodiments, the organoaluminum compound of the catalyst system may comprise, consist essentially of, or consist of any of these compounds.

Without intending to be bound by theory, the alky aluminum compound may be operable to remove impurities, or poisons that may have a negative effect on the catalyst. Additionally, the alkyl aluminum compound may be operable to alkylate the chromium compound. Furthermore, the alkyl aluminum compound may be operable to activate the chromium compound to allow the coordination of the ethylene with the catalyst.

In one or more embodiments, the catalyst system may include the co-catalyst in an amount such that a molar ratio of aluminum to chromium in the catalyst system is from 1 to 5000.

In one or more embodiments, ethylene may be contacted with the catalyst system to from a reaction product including 1-octene. Contacting may generally include any mixing and/or combining of the reactant ethylene with the catalyst system. In some embodiments, the catalyst and co-catalyst may be separately prepared as solutions, and then combined, prior to contacting of the catalyst system with ethylene. In some embodiments, the catalyst system may be contacted with ethylene in the presence of one or more reaction mediums. Suitable reaction mediums may include, for example, cyclohexane and chlorobenzene. In some embodiments, the ethylene may be contacted with the catalyst system in the presence of hydrogen.

In one or more embodiments, the reaction may be performed as a batch reaction or as a continuous process reaction, such as a continuous stir tank reactor process. In some embodiments, the pressure of the reactor may be from 2 bar to 120 bar (such as from 10 bar to 50 bar), and the reactor temperature may be from 30° C. to 120° C. (such as from 30° C. to 75° C.). However, process conditions outside of these ranges are contemplated, especially in view of the specific design of the reactor system and concentrations of the reactants and catalyst system.

It should be understood that, in one or more embodiments, similar catalyst systems that do not include the ligand of the present application may exhibit increased fouling compared to the catalyst system of the present application. In one or more embodiments, the inclusion of the ligand in a catalyst system may suppress polymer formation while not greatly reducing the yield of 1-octene. In one or more embodiments, polymer formation (fouling) may be reduced by at least 5% or hither by the use of the ligand. For example, the reaction product of the tetramerization of ethylene using the catalyst system may include less than 99 wt. % to less than 3 wt. % of polymer.

In one or more embodiments, 1 octene production may be increased, stay the same, or may decrease by less than or equal to 100% to 5% by the inclusion of the ligand. For example, the reaction product of the tetramerization of ethylene using the catalyst system may include from greater than 5 wt. % to 100 wt. % of 1-octene.

In one or more embodiments, the catalyst system may both reduce the polymer formation from 0.5% to 99.9% and increase, not effect, or decrease 1-octene production rate by less than or equal to 100% to 5%. Reduction in polymer formation rates and catalytic activity on a percentage basis are based on catalyst systems that include the ligand of the present disclosure as compared with catalyst systems that do not include the ligand of the present disclosure.

In one or more embodiments, the catalyst system may have increased activity compared to similar catalyst systems that do not include the ligand of the present disclosure. As used in the present disclosure, the term "activity" refers to the amount of reaction product produced (in kilograms) per the amount of chromium metal used (in grams) per hour ($kg \cdot g_{Cr}^{-1} \cdot h^{-1}$). In some embodiments, the catalyst system may have an activity greater than $10 \text{ kg} \cdot g_{Cr}^{-1} \cdot h^{-1}$, or greater than $100 \text{ kg} \cdot g_{Cr}^{-1} \cdot h^{-1}$ to $5{,}000 \text{ kg} \cdot g_{Cr}^{-1} \cdot h^{-1}$.

Examples

The various aspects of the present disclosure will be further clarified by the following examples. The examples are illustrative in nature and should not be understood to limit the subject matter of the present disclosure.

Preparation of $C_6H_4(m\text{-}CF_3)N(PPh_2)_2$

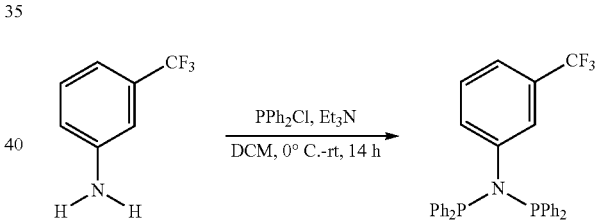

First, $Ph_2PCl$ (4.00 grams; 18.30 millimoles (mmol)) was slowly added to a solution of $C_6H_4(m\text{-}CF_3)NH_2$ (1.46 grams, 9.10 mmol) and $(C_2H_5)_3N$ (2.54 grams, 25.11 mmol) in $CH_2Cl_2$ (20 milliliters (ml)) at 0 degrees Celsius (° C.). The resulting mixture was then stirred at 0° C. for 1 hour before being warmed to room temperature and stirred for an additional 14 hours. Volatiles were then removed under reduced pressure and the remaining reside was extracted with anhydrous tetrahydrofuran (THF). The THF was then removed and the resulting solid residue was triturated with dry $CH_3CN$ and vacuum dried at 50° C. for 6 hours to yield $C_6H_4(m\text{-}CF_3)N(PPh_2)_2$ (63% yield). It should be noted that the entire preparation was performed under an inert atmosphere of dry argon using standard Schlenk techniques.

$^1$H NMR ($C_6D_6$): δ 8.03-6.50 (m, aromatic H) ppm; $^{31}$P NMR ($C_6D_6$): δ 67.47 ppm (s).

Elemental Microanalysis: Calculated (%) for $C_{31}H_{24}F_3NP_2$: H, 4.57, C, 70.32, N, 2.65; Found (%): H, 3.65, C, 70.75, N, 2.73.

Ethylene Tetramerization

Multiple ethylene tetramerization runs were performed in a magnetically stirred (1000 rotations per minute (rpm)) stainless steel reactor system (250 ml; commercially available from Buchi), which was equipped with a propeller-like stirrer and injection barrel for charging solvents and reagents. The reactor system was first heated to 110° C., purged several times with argon and ethylene to remove air and moisture, and then cooled to the desired temperature. A solution of the co-catalyst (methylaluminoxane (MAO), modified methylaluminoxane (MMAO), triisobutylaluminium (TiBA), or combinations of these) was then prepared via dilution with a suitable solvent to a total volume of 95 ml. Next, a catalyst solution was prepared when $Cr(acac)_3$ and $C_6H_4(m-CF_3)N(PPh_2)_2$ were separately dissolved in a solvent (1 ml each) before being combined and diluted to a total volume of 5 ml. In examples where the reaction medium was cyclohexane (CyH), the solvent of the catalyst solution was either toluene or chlorobenzene. The co-catalyst and catalyst solutions were transferred to the reactor system, which was then pressurized to 45 bar using ethylene to initiate ethylene tetramerization. The temperature of the reactor system was maintained constant during ethylene tetramerization by circulating relatively warm oil through a jacket of the reactor system and relatively cool liquid through a cooling coil of the reactor system as necessary.

After 10 minutes, methanol (1.0 ml) was added to quench ethylene tetramerization. The reactor system was then cooled to approximately 15° C. and slowly depressurized using a needle valve. Next, an aliquot of the liquid inside the reaction system was collected and quantified via gas chromatography (GC) analysis. The liquid remaining in the reaction system was collected, added to acidic methanol (50 ml, 5% HCl), and stirred at room temperature for 2 hours. Polymer was then filtered from the mixture, washed with distilled water, and stirred in water (200 ml) for 1 hour. This process was repeated four times. Finally, the polymer was filtered and dried in a vacuum oven at 60° C. overnight.

The conditions and results of each run are reported in Table 1.

$R_4$ are independently chosen hydrocarbyl groups or heterohydrocarbyl groups.

A second aspect of the present disclosure may include the first aspect, where one or more of $R_1$, $R_2$, $R_3$ and $R_4$ are substituted or unsubstituted aryl moieties.

A third aspect of the present disclosure may include either of the first or second aspects, where the ligand has a chemical structure according to Formula (X). In Formula (X), each Ar is independently chosen from a substituted or unsubstituted aryl group; $R_6$, $R_7$, $R_8$, $R_9$, and $R_{10}$ are each independently chosen from hydrogen or a substituted or unsubstituted hydrocarbyl group; and one or more of $R_6$, $R_7$, $R_8$, $R_9$, and $R_{10}$ are groups represented formulaically as $C_nF_{2n+1}$ or as $SiZ_3$, where each Z is independently chosen from a substituted or unsubstituted hydrocarbyl group or a substituted or unsubstituted heterohydrocarbyl group.

A fourth aspect of the present disclosure may include the third aspect, where one or more of $R_6$, $R_7$, $R_8$, $R_9$, and $R_{10}$ are groups represented formulaically as $C_nF_{2n+1}$.

A fifth aspect of the present disclosure may include the third aspect, where one or more of $R_6$, $R_7$, $R_8$, $R_9$, and $R_{10}$ are groups represented formulaically as $SiZ_3$, where each Z is independently chosen from a substituted or unsubstituted hydrocarbyl group.

A sixth aspect of the present disclosure may include the third aspect, where one or more of $R_7$ and $R_9$ are groups represented formulaically as $C_nF_{2n+1}$ or as $SiZ_3$, where each Z is independently chosen from a substituted or unsubstituted hydrocarbyl group.

A seventh aspect of the present disclosure may include any of the first through sixth aspects, where the catalyst comprises the ligand in an amount such that a molar ratio of the ligand to chromium is from 0.1 to 10.0.

An eighth aspect of the present disclosure may include any of the first through seventh aspects, where the chromium compound comprises one or more of an organic chromium

TABLE 1

| Example | °C. | Solvent | Co-Catalyst | $Cr(acac)_3$ (μmol) | Molar Ratio (Al:Cr) | Molar Ratio (L:Cr) | Activity ($kg \cdot g_{Cr}^{-1} \cdot h^{-1}$) | 1-Hexne (wt. %) | 1-Octene (wt. %) | Polymer (wt. %) |
|---|---|---|---|---|---|---|---|---|---|---|
| 1 | 30 | CyH | MMAO-3A | 2.0 | 1000 | 1.0 | 12 | 11.9 | 58.6 | 12.7 |
| 2 | 45 | CyH | MMAO-3A | 2.0 | 1000 | 1.0 | 116 | 10.2 | 69.4 | 2.0 |
| 3 | 45 | CyH | MMAO-3A | 2.0 | 1000 | 1.2 | 118 | 11.7 | 69.3 | 2.8 |
| 4 | 60 | CyH | MMAO-3A | 2.0 | 1000 | 1.0 | 236 | 11.4 | 73.2 | 0.8 |
| 5 | 75 | CyH | MMAO-3A | 2.0 | 1000 | 1.0 | 315 | 18.1 | 69.4 | 0.5 |
| 6 | 75 | CyH | MMAO-3A | 1.0 | 1000 | 1.0 | 551 | 18.6 | 69.1 | 0.1 |
| 7 | 75 | CyH | MMAO-3A | 2.0 | 2000 | 1.0 | 789 | 14.3 | 68.4 | 0.9 |
| 8 | 75 | CyH | MMAO-3A | 2.0 | 2000 | 1.0 | 700 | 20.2 | 67.8 | 0.2 |
| 9 | 90 | CyH | MMAO-3A | 2.0 | 1000 | 1.0 | 208 | 22.0 | 59.0 | 3.7 |
| 10 | 45 | PhCl | MMAO-3A | 1.0 | 2000 | 1.0 | 1492 | 13.5 | 69.0 | 0.8 |
| 11 | 60 | PhCl | MMAO-3A | 1.0 | 2000 | 1.0 | 1852 | 20.6 | 67.7 | 0.7 |
| 12 | 75 | PhCl | MMAO-3A | 1.0 | 2000 | 1.0 | 2187 | 31.0 | 59.5 | 0.8 |
| 13 | 75 | CyH | MMAO-3A/TiBA (10:1) | 1.0 | 2000 | 1.0 | 231 | 19.5 | 68.0 | 0.4 |
| 14 | 75 | CyH | MMAO-12 | 1.0 | 2000 | 1.0 | 213 | 20.5 | 57.8 | 2.1 |
| 15 | 75 | CyH | MAO | 1.0 | 2000 | 1.0 | 228 | 20.0 | 64.7 | 4.1 |

In a first aspect of the present disclosure, a catalyst system suitable for tetramerizing ethylene to form 1-octene may include a catalyst including a chromium compound coordinated with a ligand and a co-catalyst comprising an organoaluminum compound. The ligand has a chemical structure: $(R_1)(R_2)A-X-C(R_3)(R_4)$. A and C are phosphorus. X is $B(R_5)$, $Si(R_5)_2$, $N(R_5)$, wherein $R_5$ is an aryl group substituted with a halogen, halogenated alkyl or a silyl group, and wherein B, or N, or Si is bound to A and C. $R_1$, $R_2$, $R_3$, and salt, an inorganic chromium salt, a chromium coordination, and a chromium organometallic complex.

A ninth aspect of the present disclosure may include any of the first through eighth aspects, where the chromium compound comprises one or more of chromium trichloride tris-tetrahydrofuran complex, (benzene)tricarbonyl chromium, chromium (III) octanoate, chromium (III) acetylacetonate, chromium hexacarbonyl, and chromium (III) 2-ethylhexanoate.

A tenth aspect of the present disclosure may include any of the first through ninth aspects, where the organoaluminum compound has a structure of Formula (XI). In Formula (XI), $R_{11}$, $R_{12}$, and $R_{13}$ are each selected from a hydrogen atom and a ($C_1$-$C_{20}$) hydrocarbyl group or a ($C_1$-$C_{20}$) heterohydrocarbyl group.

An eleventh aspect of the present disclosure may include any of the first through tenth aspects, where the organoaluminum compound comprises one or more of trimethylaluminium, triethylaluminum, tripropylaluminum, tri-iso-butylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane, ethylaluminoxane, and modified methylaluminoxane.

A twelfth aspect of the present disclosure may include any of the first through eleventh aspects, where the catalyst system comprises the co-catalyst in an amount such that a molar ratio of aluminum to chromium is from 1 to 5000.

According to a thirteenth aspect of the present disclosure, a method for tetramerizing ethylene to form 1-octene may include contacting ethylene with the catalyst system of any of the first through twelfth aspects to form a product comprising 1-octene.

A fourteenth aspect of the present disclosure may include the thirteenth aspect, where the ethylene is formed in conditions of a reactor pressure from 5 bar to 120 bar and a reactor temperature from 25° C. to 180° C.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

For the purposes of describing and defining the present disclosure it is noted that the terms "about" or "approximately" are utilized in this disclosure to represent the inherent degree of uncertainty that may be attributed to any quantitative comparison, value, measurement, or other representation. The terms "about" and/or "approximately" are also utilized in this disclosure to represent the degree by which a quantitative representation may vary from a stated reference without resulting in a change in the basic function of the subject matter at issue.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" a second component, it is contemplated that, in some embodiments, the first component "consists" or "consists essentially of" that second component. It should further be understood that where a first component is described as "comprising" a second component, it is contemplated that, in some embodiments, the first component comprises at least 10%, at least 20%, at least 30%, at least 40%, at least 50%, at least 60%, at least 70%, at least 80%, at least 90%, at least 95%, or even at least 99% that second component (where % can be weight % or molar %).

Additionally, the term "consisting essentially of" is used in this disclosure to refer to quantitative values that do not materially affect the basic and novel characteristic(s) of the disclosure. For example, a chemical composition "consisting essentially" of a particular chemical constituent or group of chemical constituents should be understood to mean that the composition includes at least about 99.5% of a that particular chemical constituent or group of chemical constituents.

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a composition should be appreciated as containing, in some embodiments, a mixture of isomers of that constituent. In additional embodiments, the chemical compounds may be present in alternative forms such as derivatives, salts, hydroxides, etc.

What is claimed is:

1. A catalyst system suitable for tetramerizing ethylene to form 1-octene, the catalyst system comprising:
    a catalyst comprising a chromium compound coordinated with a ligand; and
    a co-catalyst comprising an organoaluminum compound, wherein:
        the ligand has a chemical structure: $(R_1)(R_2)A$-$X$-$C(R_3)(R_4)$;
        A and C are phosphorus;
        X is $B(R_5)$, $Si(R_5)_2$, or $N(R_5)$, wherein $R_5$ is an aryl group substituted with a halogenated alkyl or a silyl group, and wherein the B, the N, or the Si is bound to A and C; and
        $R_1$, $R_2$, $R_3$, and $R_4$ are independently chosen hydrocarbyl groups or heterohydrocarbyl groups.

2. The catalyst system of claim 1, wherein one or more of $R_1$, $R_2$, $R_3$, and $R_4$ are substituted or unsubstituted aryl moieties.

3. The catalyst system of claim 1, wherein the ligand has a chemical structure:

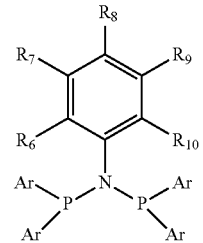

wherein:
    each Ar is independently chosen from a substituted or unsubstituted aryl group;
    $R_6$, $R_7$, $R_8$, $R_9$, and $R_{10}$ are each independently chosen from hydrogen or a substituted or unsubstituted hydrocarbyl group; and
    one or more of $R_6$, $R_7$, $R_8$, $R_9$, and $R_{10}$ are groups represented formulaically as $C_nF_{2n+1}$ or as $SiZ_3$, where each Z is independently chosen from a substituted or unsubstituted hydrocarbyl group or a substituted or unsubstituted heterohydrocarbyl group.

4. The catalyst system of claim 3, wherein one or more of $R_7$ and $R_9$ are groups represented formulaically as $C_nF_{2n+1}$ or as $SiZ_3$, where each Z is independently chosen from a substituted or unsubstituted hydrocarbyl group.

5. The catalyst system of claim 1, wherein the catalyst comprises the ligand in an amount such that a molar ratio of the ligand to chromium is from 0.1 to 10.0.

6. The catalyst system of claim 1, wherein the chromium compound comprises one or more of an organic chromium salt, an inorganic chromium salt, a chromium coordination, and a chromium organometallic complex.

7. The catalyst system of claim 1, wherein the chromium compound comprises one or more of chromium trichloride tris-tetrahydrofuran complex, (benzene)tricarbonyl chromium, chromium (III) octanoate, chromium (III) acetylacetonoate, chromium hexacarbonyl, and chromium (III) 2-ethylhexanoate.

8. The catalyst system of claim 1, wherein the organoaluminum compound has a structure:

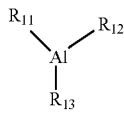

wherein $R_{11}$, $R_{12}$, and $R_{13}$ are each selected from a hydrogen atom and a $(C_1-C_{20})$ hydrocarbyl group or a $(C_1-C_{20})$ heterohydrocarbyl group.

9. The catalyst system of claim 1, wherein the organoaluminum compound comprises one or more of trimethylaluminium, triethylaluminum, tripropylaluminum, tri-isobutylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane, ethylaluminoxane, and modified methylaluminoxane.

10. The catalyst system of claim 1, wherein the catalyst system comprises the co-catalyst in an amount such that a molar ratio of aluminum to chromium is from 1 to 5000.

11. A method for tetramerizing ethylene to form 1-octene, the method comprising contacting ethylene with the catalyst system of claim 1 to form a product comprising 1-octene.

12. The method of claim 11, wherein the ethylene is formed in conditions of:
a reactor pressure from 5 bar to 120 bar; and
a reactor temperature from 25° C. to 180° C.

13. A catalyst system suitable for tetramerizing ethylene to form 1-octene, the catalyst system comprising:
a catalyst comprising a chromium compound coordinated with a ligand; and
a co-catalyst comprising an organoaluminum compound, wherein the ligand has a chemical structure:

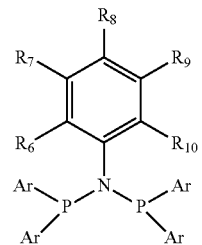

wherein:
each Ar is independently chosen from a substituted or unsubstituted aryl group;
$R_6$, $R_7$, $R_8$, $R_9$, and $R_{10}$ are each independently chosen from hydrogen or a substituted or unsubstituted hydrocarbyl group; and
one or more of $R_6$, $R_7$, $R_8$, $R_9$, and $R_{10}$ are groups represented formulaically as $C_nF_{2n+1}$ or as $SiZ_3$, where each Z is independently chosen from a substituted or unsubstituted hydrocarbyl group or a substituted or unsubstituted heterohydrocarbyl group.

14. The catalyst system of claim 13, wherein one or more of $R_7$ and $R_9$ are groups represented formulaically as $C_nF_{2n+1}$ or as $SiZ_3$, where each Z is independently chosen from a substituted or unsubstituted hydrocarbyl group.

15. The catalyst system of claim 13, wherein the catalyst comprises the ligand in an amount such that a molar ratio of the ligand to chromium is from 0.1 to 10.0.

16. The catalyst system of claim 13, wherein the chromium compound comprises one or more of an organic chromium salt, an inorganic chromium salt, a chromium coordination, and a chromium organometallic complex.

17. The catalyst system of claim 13, wherein the chromium compound comprises one or more of chromium trichloride tris-tetrahydrofuran complex, (benzene)tricarbonyl chromium, chromium (III) octanoate, chromium (III) acetylacetonoate, chromium hexacarbonyl, and chromium (III) 2-ethylhexanoate.

18. The catalyst system of claim 13, wherein the organoaluminum compound has a structure:

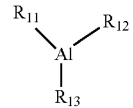

wherein $R_{11}$, $R_{12}$, and $R_{13}$ are each selected from a hydrogen atom and a $(C_1-C_{20})$ hydrocarbyl group or a $(C_1-C_{20})$ heterohydrocarbyl group.

19. The catalyst system of claim 13, wherein the organoaluminum compound comprises one or more of trimethylaluminium, triethylaluminum, tripropylaluminum, tri-isobutylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane, ethylaluminoxane, and modified methylaluminoxane.

20. The catalyst system of claim 13, wherein the catalyst system comprises the co-catalyst in an amount such that a molar ratio of aluminum to chromium is from 1 to 5000.

* * * * *